(12) United States Patent
Mukhopadhyay et al.

(10) Patent No.: US 8,519,154 B2
(45) Date of Patent: Aug. 27, 2013

(54) METHOD FOR TREATMENT OF BRONCHIAL ASTHMA

(75) Inventors: Sibabrata Mukhopadhyay, Kolkata (IN); Mumu Chakraborty, Kolkata (IN); Tulika Mukherjee, Kolkata (IN); Arun Bandyopadhyay, Kolkata (IN); Dipak Kar, Kolkata (IN); Tanima Banerjee, Kolkata (IN); Aditya Konar, Kolkata (IN); Debaprasad Jana, Kolkata (IN); Siddhartha Roy, Kolkata (IN); Santu Bandyopadhyay, Kolkata (IN); Balram Ghosh, Delhi (IN); Mabalirajan Ulaganathan, Delhi (IN); Rakesh Kamal Johri, Jammu (IN); Subhash Chander Sharma, Jammu (IN); Gurdarshan Singh, Jammu (IN); Bholanath Paul, Lucknow (IN); Vasanta Madhava Sharma Gangavaram, Hyderabad (IN); Jhillu Singh Yadav, Hyderabad (IN); Radha Krishna Palakodety, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/365,979

(22) Filed: Feb. 3, 2012

(65) Prior Publication Data

US 2012/0202868 A1   Aug. 9, 2012

(30) Foreign Application Priority Data

Feb. 4, 2011   (IN) .............................. 267/DEL/2011

(51) Int. Cl.
*C07D 209/82* (2006.01)
*C07D 209/88* (2006.01)
*A61K 31/403* (2006.01)

(52) U.S. Cl.
USPC ........... 548/441; 548/444; 548/445; 548/446; 514/411

(58) Field of Classification Search
None
See application file for complete search history.

(56) References Cited

PUBLICATIONS

Adebajo et al Journal of Ethnopharmacology 122 (2009) 10-19.*
Adebajo et al Phytomedicine 13(4) (2006): 246-254.*

* cited by examiner

*Primary Examiner* — Nyeemah A Grazier
(74) *Attorney, Agent, or Firm* — Sughrue Mion, PLLC (57) ABSTRACT

The present invention relates to a method for the treatment of bronchial asthma and chronic obstructive pulmonary disease (COPD) comprising administering to the patient suffering from asthma and COPD an effective dose of carbazole derivatives or salt thereof, optionally along with pharmaceutically acceptable excipients.

Structural formula of the compounds of general formula 1 useful as phosphodiesterase-4 (PDE-4) enzyme inhibitors, inhibitor for signalling molecule for the treatment of asthma and asthma related diseases is given below:

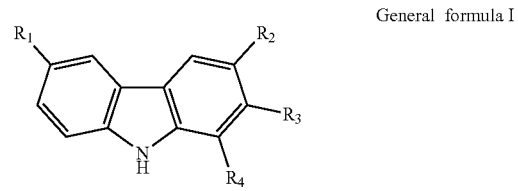

General formula I wherein $R_1$=H or $OCH_3$; $R_2$=$CH_3$ or CHO; $R_3$=H or $OCH_3$; $R_4$=H or $OCH_3$ Herbal route for the isolation of compound of general formula 1 from the bark of plant *Murraya Koenigii* and chemical route for the preparation of such compounds from basic compounds such as vanillin is also reported.

8 Claims, 6 Drawing Sheets

Scheme 1

Scheme 1a

Veh. Control          187mg/kg Compound I ( ICB/11/D-8)

Figure 6A

Vehicle Control          187mg/kg Compound (I ICB/11/D-8)          93 mg/kg Compound (I ICB/11/D-8)

Figure 6B

METHOD FOR TREATMENT OF BRONCHIAL ASTHMA

FIELD OF THE INVENTION

The present invention relates to a method for the treatment of bronchial asthma and chronic obstructive pulmonary disease (COPD). The present invention further relates to a method comprising administering to the patient suffering from asthma and COPD an effective dose of carbazole derivatives or salt thereof, optionally along with pharmaceutically acceptable excipients.

Particularly, present invention further relates to compounds of general formula 1 useful as phosphodiesterase-4 (PDE-4) enzyme inhibitors, inhibitor for signalling molecule for the treatment of asthma and asthma related diseases.

More particularly, the present invention further describes herbal route for the isolation of compound of general formula 1 from the bark of plant *Murraya Koenigii* and chemical route for the preparation of such compounds from basic compounds such as vanillin.

BACKGROUND AND PRIOR ART OF THE INVENTION

Asthma is a non-infectious chronic inflammatory disease of the respiratory system characterized by a reversible airways obstruction. Acute airway obstruction, bronchial hyperresponsiveness and inflammatory state of the bronchial mucosa with increase levels of inflammatory mediators, are the most evident phenomenon which characterizes this pathology. Despite the increase in the prescribed anti-asthmatic treatments, the current trends indicate asthma is set to be the most chronic disease in industrialized countries, affecting mostly the children (10%) than the adults (15%).

Chronic obstructive pulmonary disease (COPD) is the most common of all the respiratory disorders in the world, which embraces several inflammatory pathologies that often co-exist. The WHO predicts COPD (Donnelly, L. E.; Rogers, D. F., Therapy for COPD in the 21$^{st}$ century, *Drugs*, 63, 1973-1998, 2003) will become the third most common cause of death world over by 2020 accounting 8.4 million lives. Although asthma for the last 25 years has been managed therapeutically, with a combined bronchodilator and anti-inflammatory therapies, in contrast to this COPD have no effective treatments currently, while the efficacy of the corticosteroids is controversial. Hence, there is an urgent need to develop novel anti-inflammatory drugs having both the bronchodilatory and anti-inflammatory activity, having applicability to treat both COPD as well as asthma. Thus, the development of therapies for bronchial asthma has become the major focus of the pharmaceutical industry in the field of respiratory disorders.

References may be made to journals Yeoung, K,-P; *Drug Discovery Today* 14, 812-813, 2009; Houslay, M. D.; Schafer, P.; Zhang, K, Y, J. *Drug Discovery Today* 10, 1503-1519, 2005; Dal Piaz, V.; Giovannoni, M. P., *Eur. J. Med. Chem.*, 35, 463-480, 2000; Giembycz, M. A. *Monaldi Arch Chest Dis.* 57, 48-64, 2002; Molfino, N. A., *Respiration* 72, 105-112, 2005; Conti, M.; Beavo, J. *Annu. Rev. Biochem.*, 76, 481-511, 2007, wherein development of novel PDE-4 inhibitors and its therapeutic applications was reported. PDEs are a large family of enzymes that metabolise the second messenger cAMP/cGMP into inactive acyclic systems. The role of cAMP as a second messenger is well established and it modulates the response of immune cells to a variety of stimuli. Elevation of cAMP has generally been associated with inhibition of lymphocyte activity. The elevation of cAMP levels leads to the suppression of the synthesis and release of pro-inflammatory signals, cytokines and inhibit the production of reactive oxygen species.

The PD enzymes are a large family with eleven sub-families. Of these, the PDE-4, 7 and 8 are associated with the metabolism of cAMP. PDE-4 has four distinct genes, PDE-4A, PDE-4B, PDE-4C and PDE-4D (Muller, T.; Engels, P.; Fozard, J. R. *Trends Pharmacol. Sci.*, 17, 294-298, 1996) with specificity to cAMP and thus have become potential therapeutic targets and most of the research is centred on PDE-4 inhibitors (Teixeira, M. M.; Gristwood, R. W.; Cooper, N.; Hellewell, P. G. PDE-4 inhibitors: *Trends Pharmacol. Sci.*, 18, 164-170, 1997). PDE-4 is the selective phosphodiesterase enzyme that metabolises the cAMP. Hence, PDE-4 inhibitors prevent the inactivation of cAMP.

The presence of PDE 4 inhibitor in natural product has also been reported earlier. Mesembrine, a major alkaloid present in *Selectium torouosum*, has been shown to act as a PDE-4 inhibitor (Smith, M.; Crouch, N.; Gericke, N.; Hirst, M. Psychoactive constituents of the genus *Sceletium* N.E.Br. and other Mesembryanthemaceae: review. *J. Ethnopharmacol* 50, 119-30, 1996; Pharmaceutical compositions containing mesembrine and related compounds. U.S. Pat. No. 6,288, 104). This is the first catechol based natural product that showed PDE-4 activity. Theophylline is the oldest and shows a weak and non-specific PDE inhibition. Rolipram is the most effective PDE-4 inhibitor, since its discovery, (Griswold, D. E.; Webb, E. F.; Breton, J.; White, J. R.; Marshall, P. J.; Torphy, T. J., Effect of selective phosphodiesterase type IV inhibitor, rolipram, on fluid and cellular phases of inflammatory response, *Inflammation* 17, 333-44, 1993; Schneider, H. H.; Schmiechen, R.; Brezniski, M.; Seidler, J.; *Eur. J. Pharmocol.*, 127, 105-115, 1986). It is a catechol based compound and structurally related to mesembrine. Rolipram, thus has become a template for the synthesis of novel inhibitors, besides becoming a reference drug in evaluating other inhibitors. Ariflo (cilomilast, SB-207,499; Profita, M, Chiappara G, Mirabella, F Chimenti, G Di, L, Costanzo, G, Riccobono, L Bellia V, Bousquet J, and Vignola A. Effect of cilomilast (Ariflo) on TNF-, IL-8 and GM-CSF release by airway cells of patients with COPD. 58, 573-579, 2003. Ochiai, H.; Ohtani, T.; Ishida, A.; Kusumi, K.; Kato, M.; Kohno, H.; Kishikawa, K.; Obata, T.; Nakai, H.; Toda, M. *Bioorg. Med. Chem. Lett.*, 14, 207-10, 2004), roflumilast (Hatzelmann, A.; Schudt, C. *J. Pharmacol. Exp. Ther.* 297, 267-290, 2001), CDP-840, HT-0712, filaminast are some of the rolipram related active PDE-4 molecules, while V-11294A which is in phase-II clinical trials represents a hybrid molecule of xanthine and rolipram. Cilomilast, roflumilast, BAY-19-8004 and arofylline are in phase-III clinical trials. Thus, PDE4 appears an important target for COPD also.

However the most common and worrisome aspect in the PDE-4 inhibitors is their propensity for side effects such as nausea and vomiting. The mechanisms by which the PDE-4 inhibitors induce side effects are uncertain. However, the family of PDE-4 enzymes exist in two different conformational states (Souness, J. E.; Rao, S. *Cell Signal*, 9, 227-236, 1997; Duplantier, A. J. et al., *J. Med. Chem.* 39, 120-125, 1996), distinguishable with their affinity towards rolipram: the conformation with low affinity for rolipram is LAR conformation (PDE-4L), while the one with high affinity is known as HAR conformation (PDE-4H). PDE-4L is associated with anti-inflammatory activity, while the PDE-4H conformation correlates with adverse effects such as emesis.

OBJECTIVES OF THE INVENTION

The main objective of the present invention is to provide a method for treatment of bronchial asthma and chronic obstructive pulmonary disease (COPD) comprising administering to the patient suffering therefrom an effective dose of compound of general formula 1 or salt thereof, optionally along with pharmaceutically acceptable excipients.

Another object of the present invention is to provide isolation of phosphodiesterase 4 (PDE-4) inhibitor from herbal source, therapeutically effective for the treatment of asthma and asthma related respiratory diseases.

Yet another object of the present invention is to determine the structure of PDE 4 inhibitor compound isolated from the herbal origin.

Yet another object of the present invention is to isolate PDE 4 inhibitor from herbal origin to overcome the problems such as emesis and vomiting associated with the known active compounds.

Yet another object of the present invention is to synthesis of PDE 4 inhibitor of herbal origin and their derivatives and their evaluation is to have more therapeutic accessibility to the compounds presented in the invention.

Yet another object of the present invention is that the PDE 4 inhibitors and their analogues will have specific PDE-4 binding capacity devoid of emetic properties.

Yet another object of the present invention is that the PDE 4 inhibitors from herbal origin and their derivatives express more than one therapeutic activity towards asthma treatment.

Still, another objective of the present invention is to provide novel process routes for the synthesis of said novel PDE 4 inhibitor that exhibit significant anti-asthma activity.

Yet another objective of the present invention is to provide novel process routes to the PDE 4 inhibitor of herbal origin using commercially available reagent and shorter chemical sequence.

Yet another objective of the invention is to provide green chemistry routes and catalytic synthetic steps for the large-scale manufacture of the said PDE 4 inhibitor and their derivatives.

Yet another objective of the present invention is to provide the said novel PDE 4 inhibitor of herbal origin, in sufficient quantities for biological evaluation under environmentally friendly process chemical routes.

Yet another objective of the present invention is to find out non-toxic PDE-4 inhibitor which might be useful for the treatment of asthma.

Yet another objective of the present invention is to inhibit the signalling pathway such as expression of intercellular adhesion molecule or vascular cell adhesion molecule which is crucial for asthma pathogenesis.

Yet another objective of the present invention is to find out the compound that inhibits asthma in vivo.

SUMMARY OF THE INVENTION

Accordingly, present invention provides a method for treatment of bronchial asthma and chronic obstructive pulmonary disease (COPD) comprising administering to patient suffering therefrom an effective dose of compound of general formula 1 or salt thereof, optionally along with pharmaceutically acceptable excipients General formula I wherein
$R_1$=H or $OCH_3$;
$R_2$=CHO, $CH_3$, $CH_2OH$ or $CH_2OAC$;
$R_3$=H or $OCH_3$;
$R_4$=H, OH or $OCH_3$.

In an embodiment of the present invention, representative compounds of general formula 1 are:

Compound I 1-methoxy-3-formylcarbazole

Compound II 3-methyl-6-methoxycarbazole

Compound III 1-methoxy-3-hydroxymethylcarbazole

Compound IV 1-hydroxy-3-formylcarbazole

Compound V 1-methoxy-3-methylacetoxycarbazole

Compound VI 2,6-dimethoxy-3-methylcarbazole

In yet another embodiment of the present invention, compound of general formula 1 is administrated by oral, intravenous or mucosal route.

In yet another embodiment of the present invention, the effective dosage ranges between 1 to 10 mg/Kg body weight.

In yet another embodiment of the present invention, the compound of general formula 1 inhibits phosphodiesterase-4 (PDE-4) enzyme activity in vitro upto 90% at a dose of 0.001-10 μg/ml.

In yet another embodiment of the present invention, the compound of general formula 1 is non toxic evidenced by having spontaneous motor activity, analgesic activity, charcoal powder transportation ratio, bile secretion, pentobarbitone sleeping time, blood pressure, heart rate, respiratory rate, viability of bone marrow cells, splenocyte and lymph node lymphocyte comparable that of in absence of the administration of the compound.

In yet another embodiment of the present invention, the compound of general formula 1 is obtained either from chemical origin or from herbal origin.

In yet another embodiment of the present invention, $IC_{50}$ value of compound of general formula 1 obtained by chemical origin is 50 nM.

In yet another embodiment of the present invention, $IC_{50}$ concentration of compound obtained by extraction from plants is 20 µM.

In yet another embodiment of the present invention, a process for preparation of compound of general formula 1 by chemical route comprising the steps of:

i. providing 10 to 25% $CH_2Cl_2$ solution of compound A cooled at temperature in the range of 18 to 22° C.;

Compound A wherein $R_2$=$CH_3$ or CHO; $R_3$=H or $OCH_3$; $R_4$=H or $OCH_3$;

ii. reacting cooled solution as obtained in step (i) with 100 to 180 mol % of trifluoromethanesulphonic acid ($Tf_2O$) in the presence of 220 to 360 mol % of pyridine at temperature in the range of −18 to −22° C. for period in the range of 1 to 2 hrs to obtain compound B;

Compound B wherein $R_2$=$CH_3$ or CHO; $R_3$=H or $OCH_3$; $R_4$=H or $OCH_3$;

iii. reacting compound of formula B as obtained in step (ii) with 100 to 150 mol % substituted aniline (compound D), 200 to 300 mol % $CS2CO_3$, 8 to 10 mol % $Pd(OAc)_2$ and 16 to 20 mol % 2,2'-bis(diphenylphosphino)-1,1'-binaphthyl (BINAP) in toluene at temperature in the range of 90 to 98° C. to for period in the range of 10 to 12 hrs obtain compound C;

Compound C

Compound D wherein R1=H or $OCH_3$; $R_2$=$CH_3$ or CHO; $R_3$=H or $OCH_3$; $R_4$=H or $OCH_3$;

iv. adding 8 mol % to 10 mol % $Pd(OAc)_2$ and 8 mol % to 10 mol % $K_2CO_3$ in the 8% to 15% pivalic acid solution of compound of formula C as obtained in step (iii) at temperature in the range of 110 to 120° C. for period in the range of 11 to 13 hrs to obtain compound of general formula I General formula I wherein R1=H or $OCH_3$; $R_2$=$CH_3$ or CHO; $R_3$=H or $OCH_3$; $R_4$=H or $OCH_3$.

In yet another embodiment of the present invention, the compound of general formula 1 is useful for the treatment of bronchial asthma and chronic obstructive pulmonary disease (COPD).

In yet another embodiment of the present invention, Compound of formula III is obtained by reduction of compound of formula I with $NaBH_4$.

In yet another embodiment of the present invention, Compound of formula IV is obtained by demethylation of compound of formula II using anhydrous $AlCl_3$ and dilute HCl.

In yet another embodiment of the present invention, Compound of formula V is obtained by acetylation of compound of formula III with $AcO_2$/Pyridine.

BRIEF DESCRIPTIONS OF THE DRAWINGS

FIG. 1 depicts Scheme 1 and Scheme 1a. Scheme 1 illustrates the schematic diagram of chemical synthesis of Compound of general formula 1, wherein reagent and conditions are: a) $Tf_2O$, Pyridine, −20° C., $CH_2Cl_2$; b) aniline, $CS_2CO_3$, $Pd(OAc)_2$; c) Pivalic acid, $K_2CO_3$, $Pd(OAc)_2$, $O_2$, 115° C., 12 h.

Scheme 1a illustrates the schematic diagram of chemical synthesis of Compound I, wherein reagent and conditions are a) $Tf_2O$, Pyridine, −20° C., $CH_2Cl_2$; b) aniline, $CS_2CO_3$, $Pd(OAc)_2$; c) Pivalic acid, $K_2CO_3$, $Pd(OAc)_2$, $O_2$, 115° C., 12 h.

DETAIL DESCRIPTION OF THE INVENTION

The present invention describes the method of isolation of a novel PDE 4 inhibitor, 1-methoxy-3-formyl-9H carbazole (ICB/11/D8, Compound I) from the bark of plant *Murraya koenigii*, which inhibits asthma in vivo. It describes the procedure for isolation of pure compound from the bark of *Murraya koenigii*. The pure molecule, Compound I was isolated by chromatographic separation procedure and the homogeneity of the molecule was determined by thin layer chromatograpy (TLC) using benzene:ethyl acetate=6:1 as solvent system and the structure of the compound was established by comparison of the spectroscopic data with authentic sample.

Figure 1:
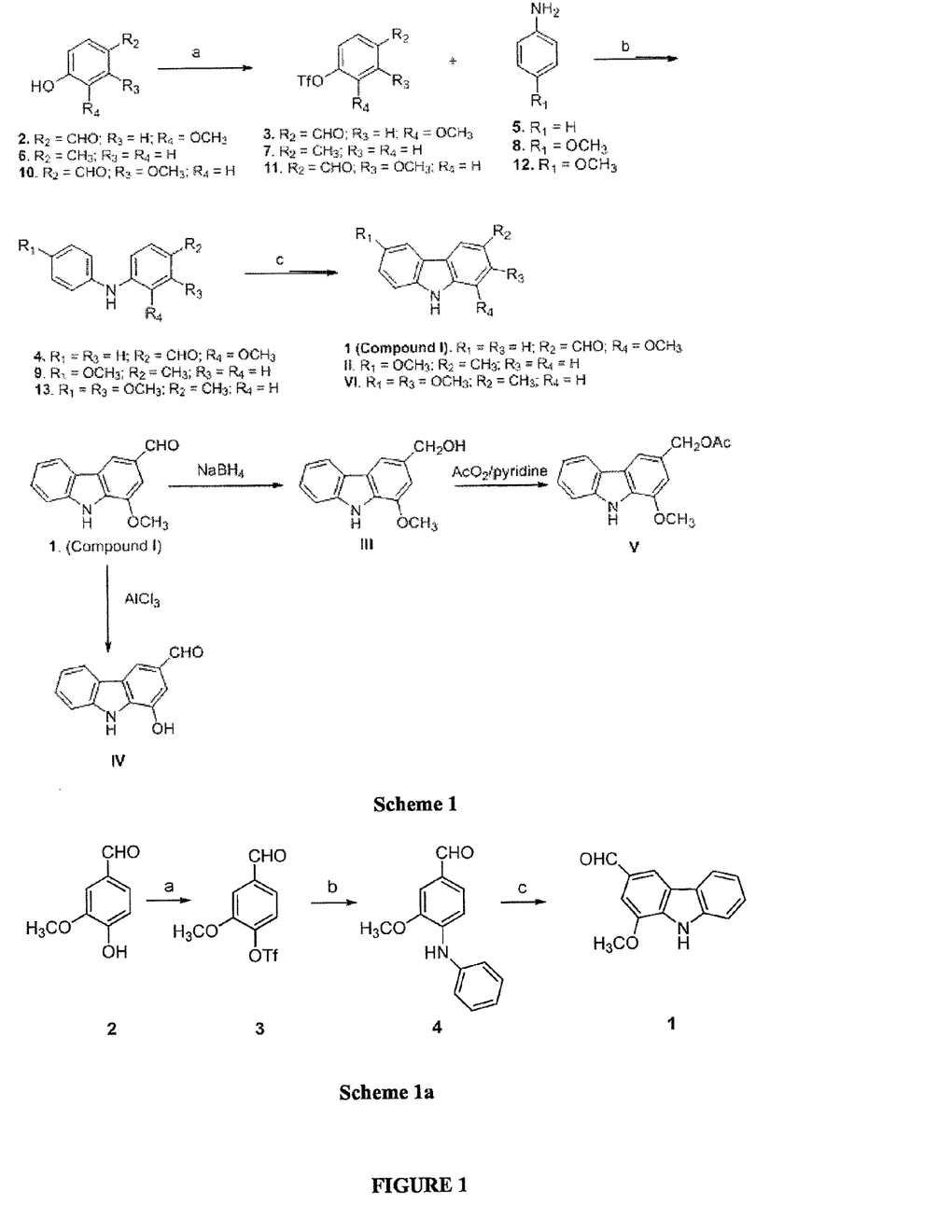

The present invention also describes methods of synthesis of above compound I which is originally isolated from *Murraya koenigii*. This natural product Compound I was synthesized from commercially available vanillin. The novel routes developed in the invention are suitable for the synthesis of compounds of the following structural Formula 1 in the steps mentioned in scheme I.

Compound I (1), a natural product was synthesized from commercially available Vanillin (2). Treatment of 2 with trifluoromethanesulfonic anhydride in the presence of pyridine at −20° C. gave the corresponding 3, which underwent coupling with aniline in the presence of $Pd(OAc)_2$ and (+/−) BINAP in toluene at 95° C. to give the desired coupled product 4. Compound 4 on reaction with $Pd(OAc)_2$ and $K_2CO_3$ in pivalic acid, gave the cyclised product 1. It also describes the analysis of the synthetic Compound I (1) by $^1H$ NMR and other spectral and analyses.

The present invention describes the methods of detection of PDE-4 activity with the compound of general formula 1 (compound I to VI) isolated from the bark of *Murraya koenigii*.

The present invention describes the method of detection of PDE 4 activity with synthetic molecule of natural origin (Compound I).

Figure 2:
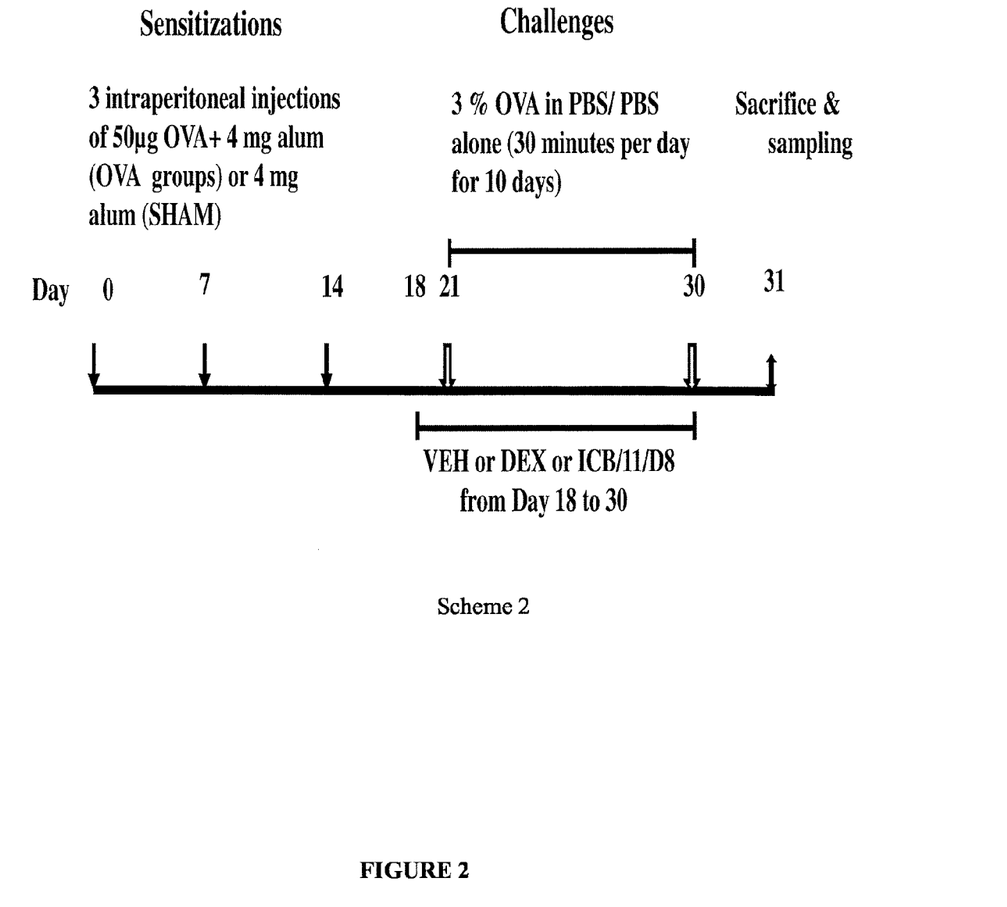
FIG. 2 depicts Scheme 2 which represent schematic diagram of In vivo efficacy test in mouse model of asthma
Figure 4A:
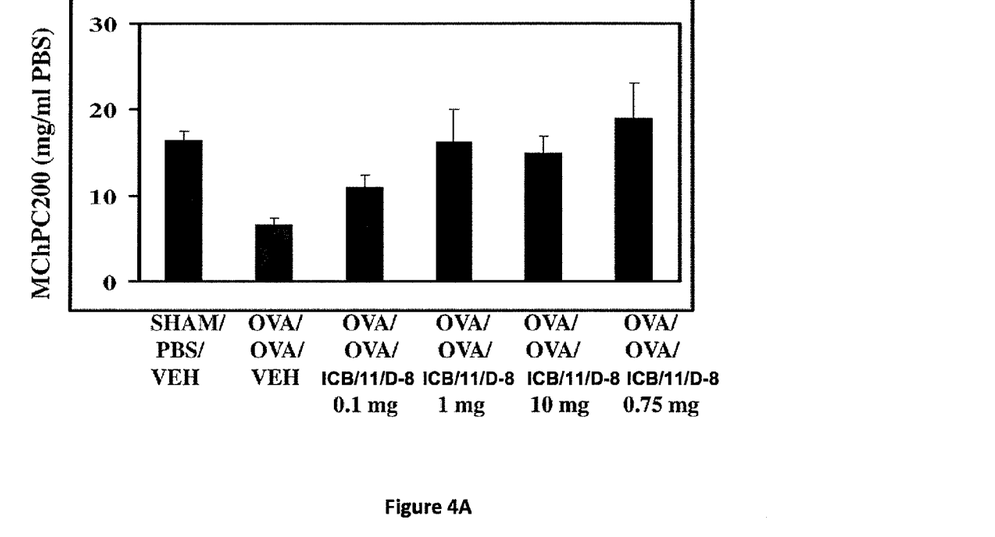
FIG. 4A illustrates inhibition of Airway hyper-responsiveness to evaluate anti-asthmatic effect in vivo by compound I
Figure 4B:
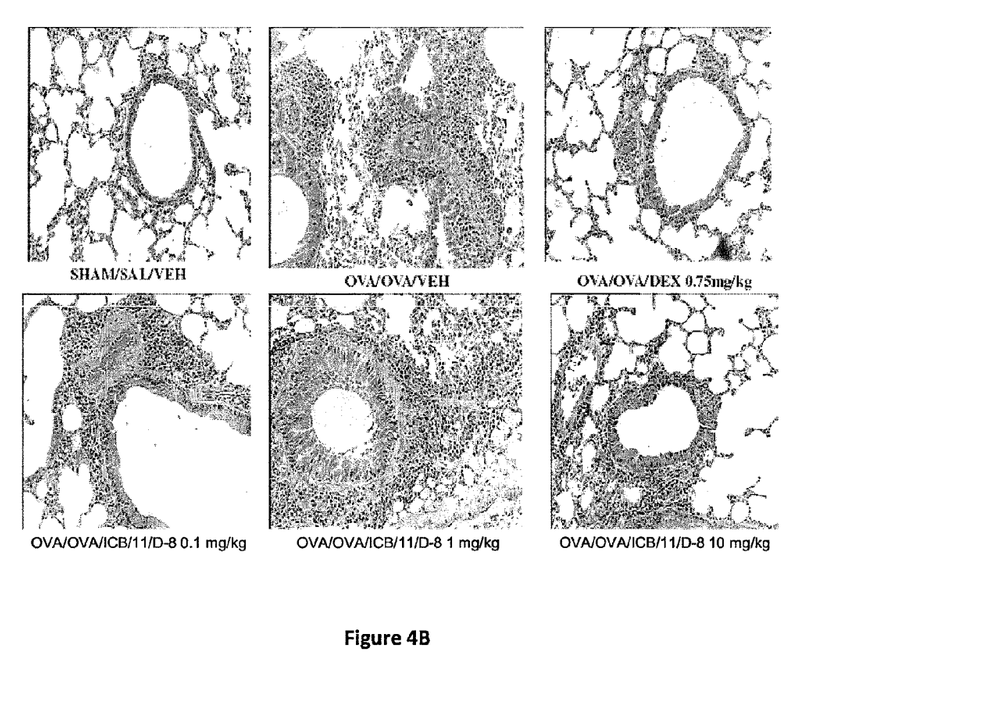
FIG. 4B illustrates anti-inflammatory effect of compound I in lung.

Present invention describes the efficacy of compound I in vivo mouse model of asthma. BALB/c mice were sensitized and challenged with ovalbumin (OVA) as shown in scheme 2 to develop asthmatic features such as airway hyperreactivity (AHR) to methacholine (MCh). The sensitized and challenged mice were treated with different concentrations of Compound I. As shown in FIG. 4, MChPC200 was decreased significantly in asthmatic controls (OVA/OVA/VEH) compared to normal control mice (SHAM/PBS/VEH). This indicates that OVA/OVA/VEH mice have developed marked bronchoconstriction. However, treatment with Compound I significantly attenuated the decrease in MChPC200 and maximum effect was found with 10 mg/kg dose (FIG. 4). This reduction was comparable with dexamethasone treatment.

The present invention also describes the inhibition of airway inflammation by Compound I in mouse model. To determine the effect of Compound I on airway inflammation, histopathological analysis of fox malin fixed, paraffin embedded lung sections was performed. Compound I treatment reduced both perivascular and peribronchial inflammation in a dose dependent manner.

The present invention also describes the method of bioavailability and pharmacokinetics of the compound I. Compound I appears to be a drug-like molecule. It crosses the intestinal barrier largely by passive diffusion. After oral administration rapid $C_{max}$ is attained (1 hr) and the significant amount of the intact drug stays in the circulation upto 12 hrs. The drug is metabolized by CYP 3A4 (liver) and negligible amounts are detected in urine after 24 hrs. D8 has good plasma clearance rate; volume of distribution is high. Compound I is highly lipophilic and showed high plasma binding.

The present invention also describes the safety pharmacology of the compound I. No significant change in blood pressure, heart rate and respiratory rate of the rats before and after the treatment of animal with the molecule.

The present invention also describes the 28 day sub acute oral toxicity profile of molecule I. 28d sub-acute oral toxicity study of Compound I was performed in mice. Few signs of toxicity were observed in mice treated with 187 mg/kg Compound I. However, no symptoms of toxicity in mice were observed in mice treated with 93 mg/kg body weight. In mice, an acute oral NOAEL and LOAEL of 93 and 187 mg/kg respectively was established based on body weight, organ weight, gross necropsy, immunotoxicity, hematology, clinical chemistry and cage side observation.

Abbreviations used are:
ICB/11/D8: Compound I (1-methoxy-3-formyl-9H carbazole)
p.o.: pre oral
i.v.: intravenous
i.m. intramucosal
i.p. Intraperitoneal

EXAMPLES

Following examples are given by way of illustration therefore should not be construed to limit the scope of the invention.

Example 1

General Procedure for the Preparation of the Compound I Isolated from *Murraya Koenigii* Bark

Barks of the plant *Murraya koenigii* (These plants were originated form Bachhurdobo, Jhargam, Paschim Medinipur, West Bengal, Pin code 721507) are dried under shade, avoiding direct sunlight. The barks are ground to obtain powder having 6/8-mesh particle size using an appropriate mill. About 1 kg of the powder is taken in a percolator and 5 liters of the solvent (distilled methanol) was added to it. At room temperature the powder of the barks is soaked in the solvent for 24 hours with frequent stirring. The contents are then filtered using cotton to obtain a clear filtrate. The process is repeated three times. The extracts are combined and processed for solvent recovery. The clear filtrate is concentrated under vacuum at 40° C. to obtain soft extract having honey-like consistency. The resulting soft extract is then dried to obtain a thick paste. The solvents are completely removed from the extract. The extract can be stored at 25° C./40% relative humidity.

Example 2

Isolation of the Pure Compound I

The methanol extract (8 gm) of the bark of *Murraya koenigii* was fractionated into three parts: petroleum ether, ethyl acetate and aqueous. The ethyl acetate part was kept overnight and filtered. The clear filtrate was chromatographed on a column of silica gel (mesh size 60-120). Gradient elution was carried out with petroleum ether (bp 60-80° C.) followed by various mixtures of petroleum ether and benzene (3:1, 1:1, 1:3 and 100% benzene) and again various mixtures of benzene and chloroform (200 ml each). Compound I was eluted with 1:1 mixture of petroleum ether and benzene. The homogeneity of the compound was determined by HPLC [RP-8 (5 um), Acetonitrile:Water (51:49) and TLC [silica gel, benzene:ethyl acetate=6:1]. The $^1$H-NMR (600 MHz, $CDCl_3$) compound exhibited a downfield singlet at δ 10.06 for the aldehydic proton, two singlets with fine splitting each integrating for one proton at δ 7.49 and 8.21 for H-2 & H-4. The three proton singlet at δ4.08 was assigned for an aromatic methoxyl protons. The four aromatic protons appeared at δ8.12 (1H, d, J=7.8 Hz, H-5), 7.32 (1H, m, H-6), 7.50 (1H, m, H-7), 7.53 (1H, m, H-8), The structure of the compound is fully corroborated with the $^{13}$C-NMR (150

MHz, CDCl$_3$): δ 191.89 (CHO), 55.81 (OMe), 146.08 (C), 103.50 (CH), 130.19 (C), 120.42 (C), 120.72 (CH), 123.63 (C), 120.72 (CH), 120.71 (CH), 126.63 (CH), 111.48 (CH), 139.38 (C), 134.05 (C). The structure of Compound I is finally established by superimposable IR spectra, MS. Co-TLC with authentic sample.

Murrayanine (compound I) ICB/11/D-8
(1-methoxy-3-formyl-9H carbazole)

Example 3

General Procedure for the Synthesis of Compound I from Vanillin

In this invention, vanillin 2 was reacted with trifluoromethanesulfonic anhydride in the presence of pyridine at −20° C. to give the corresponding trimethylsulfonate derivative 3, as shown in Scheme 1. For the exemplary reaction conditions for 3 see example 1.

Scheme 1 further exemplifies the conversion of the triflate 3 into aniline derivative 4. In the present invention, triflate 3 with the structural formula as shown in Scheme 2, was reacted with aniline in the presence of Pd(OAc)$_2$ and (+/−) BINAP in toluene at 95° C. to give the desired coupled product[2] with the formula 4. See example 2 for the exemplary reaction conditions for the preparative method of compound 4.

Scheme 1 further exemplifies the synthetic method for the conversion of the aniloine derivative 4 into the target natural product Compound I (1), whose structure is represented in Scheme 1, wherein R$_1$=R$_3$=H; R$_2$=CHO; R$_4$=OMe. As exemplified in Scheme 1, the aniline derivative 4 was, subjected to cylcization reaction in the presence of Pd(OAc)$_2$ and K$_2$CO$_3$ in pivalic acid at 115° C. to give the cyclised product 1[1,3]. The exemplary reaction conditions for the preparation of 1 are described in the example 3. The synthetic Compound I (1) was analyzed by $^1$H NMR and other spectral and analytical data. The spectral data of the synthetic product Compound I (1), prepared in the present invention and the natural product Compound I (1) isolated in the present invention were compared. The spectral and analytical data for both the natural and synthetic products of the present invention was found to be similar.

Example 4

Detail Procedure for the Synthesis of Compound I from Vanillin

Step (1)

3-Methoxy-4-trifluoromethanesulfonyloxy-benzaldehyde (3)

A stirred solution and cooled (20° C.) solution of 2 (5.0 g, 32.89 mmol) in CH$_2$Cl$_2$ (30 mL) was treated with pyridine (5.2 g, 65.82 mmol). After 15 min, Tf$_2$O (11.13 g, 39.4 mmol) was added dropwise and stirred at −20° C. for 1 h. Reaction mixture was diluted with CH$_2$Cl$_2$ (100 mL). The organic layer was washed with water (50 mL), brine (50 mL) and dried, Solvent was evaporated under reduced pressure and residue purified by column chromatography (Silica gel, 60-120 mesh, hexane:ethyl acetate 93:7) to give 3 (5.7 g, 61%) as a syrup.

Step (2)

3-methoxy-4-N-phenylamino-benzaldehyde (4)

A mixture of 3 (5.33 g, 18.76 mmol), aniline (1.74 g, 18.76 mmol), CS$_2$CO$_3$ (12.2 g, 37.5 mmol), Pd(OAc)$_2$ (0.53 g, 2.3 mmol) and (+/−) BINAP (2.92 g, 4.69 mmol) were taken in toluene (10 mL) and heated 96° C. for 12 h. Reaction mixture was cooled to room temperature, diluted with ethyl acetate (100 mL) and filtered through a pad of celite. Solvent was evaporated and residue was purified by column chromatography (Silica gel, 60-120 mesh, hexane:ethyl acetate 95:5) to afford 4 (2.8 g, 68%) as a yellow solid. $^1$H NMR (500 MHz, CDCl$_3$): δ 9.73 (s, 1H, —CHO), 7.20-7.36 (m, 7H, ArH), 7.0 (t, 1H, J=7.3 Hz, H5), 6.6 (s, 1H, —NH), 4.0 (s, -3H, —OCH$_3$).

Step (3)

1-Methoxy-9H-3-carbaolecarbaldehyde (1)

To a stirred solution of compound 4 (0.2 g, 0.88 mmol) in pivalic acid (2 mL), Pd(OAc)$_2$ (0.02 g, 0.09 mmol) and K$_2$CO$_3$ (0.01 g, 0.08 mmol) were added and heated at 115° C. for 12 h. Reaction mixture was cooled to room temperature and filtered through a pad of celite using ethyl acetate (50 mL). Organic layers were washed with saturated NaHCO$_3$ solution (20 mL), water (20 mL), brine (20 mL) and dried (Na$_2$SO$_4$). Solvent was evaporated and residue purified by column chromatography (Silica gel, 60-120 mesh, hexane:ethyl acetate 93:3) to furnish 1 (0.04 g, 20%) as a solid, mp 162-164° C. [lit.[3] mp 161-163° C.]. NMR (500 MHz, CDCl$_3$): δ 10.0 (s, 1H, —CHO), 8.5 (s, 1H, —NH), 8.15 (s, 1H, H4), 8.07 (d, 1H, J=7.5 Hz, H5), 7.3-7.5 (m, 3H, —ArH), 7.25 (s, H2), 4.09 (s, 3H, —OCH$_3$). ESI-MS: 225 (3, M$^+$), 199 (100).

Example 5

Synthesis of Compound of Formula III by Reduction of Murrayanine (Compound I) Using NaBH$_4$ 25 mg of murrayanine (compound I) was dissolved in 10 ml of distilled methanol. One pinch of NaBH$_4$ was added to it. The reaction mixture was stirred at room temperature for 24 hours using a magnetic stirrer. Progress of the reaction was monitored by TLC. Methanol was evaporated under reduced pressure. Then the product was extracted with CHCl$_3$ using a separating funnel and washed with water (3 times). Then again it was concentrated under reduced pressure. TLC (Solvent system: Benzene:EtOAc=6:1) showed the presence of a prominent spot with very little amount of impurity. The major product was purified by preparative TLC using Benzene:EtOAc=6:1 as solvent system. The structure of the product was elucidated by spectral data analysis. $^1$H-NMR (δ, CDCl$_3$, 600 MHz): 7.64 (1H, s, H-2), 8.31 (1H, s, H-4), 8.02 (1H, d, J=7.7 Hz, H-5), 7.42 (1H, m, H-6), 7.24 (1H, m, H-7), 6.94 (1H, m, H-8), 4.82 (2H, s, CH$_2$OH), 3.98 (3H, s, OCH$_3$), 3.79 (1H, s, CH$_2$OH).

Compound I

Compound III

Example 6

Synthesis of Compound of Formula IV by Demethylation of Murrayanine Using Anhydrous AlCl$_3$ 25 mg of compound I was dissolved in 15 ml of dry and distilled benzene. 1 pinch of anhydrous. AlCl$_3$ was added to it. The reaction mixture was refluxed in a water bath for 6 hours. Progress of the reaction was monitored by TLC. Benzene was evaporated under reduced pressure. The product was acidified with 15% HCl, extracted with CHCl$_3$ using a separating funnel and washed with water (3 times). Then again it was concentrated under reduced pressure. TLC (Solvent system: Benzene:EtOAc=4:1) showed the presence of a single spot. The structure of the product was elucidated by spectral data analysis. $^1$H-NMR (δ, CDCl$_3$, 600 MHz): 7.36 (1H, s, H-2), 8.21 (1H, s, H-4), 8.13 (1H, d, J=7.8 Hz, H-5), 7.25 (1H, t, J=7.6 Hz, H-6), 7.44 (1H, t, J=7.6 Hz, H-7), 7.56 (1H, d, J=8.1 Hz, H-8), 9.94 (1H, s, CHO).

Example 7

Synthesis of compound of formula V by acetylation of 1-methoxy-3-hydroxymethylcarbazole A mixture of acetic anhydride (0.02 ml) and pyridine (0.02 ml) was added to 15 mg of 1-methoxy-3-hydroxymethylcarbazole and kept it over night. TLC (Solvent system: Benzene: EtOAc=6:1) showed the presence of a single product. acetic anhydride and pyridine were removed by repeated distillation under reduced pressure with toluene. Then the product was extracted with CHCl$_3$ using a separating funnel, washed with water (3 times), dried over Na$_2$SO$_4$, filtered and concentrated under vacuum. The structure of the product was elucidated by spectral data analysis. $^1$H-NMR (δ, CDCl$_3$, 600 MHz) spectral data: 6.89 (1H, s, H-2), 7.69 (1H, s, H-4), 8.03 (1H, d, J=7.8 Hz, H-5), 7.45 (2H, m, H-6 & H-7), 7.25 (1H, m, H-8), 5.27 (2H, s, C$\underline{H}_2$OCOCH$_3$), 4.00 (3H, s, OCH$_3$), 2.12 (3H, s, CH$_2$OCOC$\underline{H}_3$).

Example 8

Determination of PDE-4 Activity In Vitro

For phosphodiesterase (PDE-4) assay, enzyme preparations were performed from rat heart (Ko et al 2004, Biochemical Pharmacology 68:2087-2094). Heart was excised from anesthetized rat and transfer into normal saline solution. Heart weighing 687 mg was taken and homogenized in 2.5 volumes of homogenization buffer containing 20 mM Tris-Cl, 50 mM NaCl, 2 mM EDTA, 0.1 mM PMSF, 1 mH DTT, protease inhibitors 1 μg/μl. The homogenate was centrifuged at 500×g for 5 minute at 4° C. Then sup was taken for further centrifuged at 40,000×g for 30 minute (ultra centrifugation). After centrifugation supernatant was collected for phosphodiesterase assay. Protein concentration was estimated and for each assay, 2.5 μg protein (PDE enzyme preparation) was used. All compounds tested for PDE 4 activity were dissolved in DMSO.

Phosphodiesterase 4 assay: Phosphodiesterase 4 assay was conducted with [$^3$H] cAMP SPA enzyme assay (GE Amersham, UK) using 2.5 μg enzyme preparation for each well. Into each well 60 μl water, 10 μl assay buffer supplied with the kit, 10 μl compound (inhibitor), 10 μl PDE enzyme or homogenizing buffer (blank) and 10 μA radiolabel led cAMP ([$^3$H] cAMP, GE Amersham, UK) were added. To check activity of the enzyme without inhibitor (compound) 10 μl DMSO was added in place of inhibitor to a separate well. The reaction mixtures were incubated for 30 ml at 30° C. The reaction was stopped by adding 50 μl SPA bead supplied with the kit. It was then mixed well and allowed to stand at room temperature for 20 min. Breakdown of cAMP in each tube was monitored by β counter. The reading in each tube was obtained in counts per minute (CPM). The reading of the blank tube (without enzyme) was subtracted from each tube to normalize the counts. The enzyme activity was calculated by considering the CPM reading without any inhibitor (compound) as 100. The results are presented in FIG. 3.

Figure 3A:
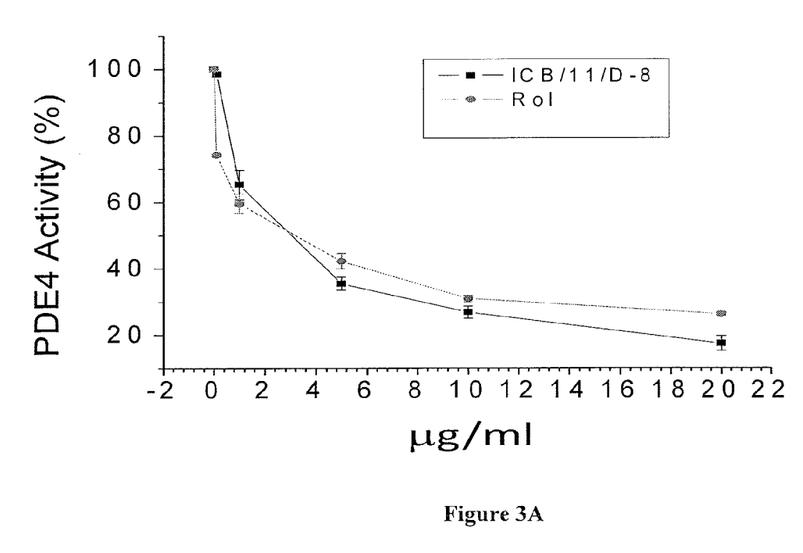
FIG. 3A illustrates the inhibition of PDE-4 activity by Compound I (1-methoxy-3-formyl-9H carbazole) (ICB/11/D-8).
Figure 3B:
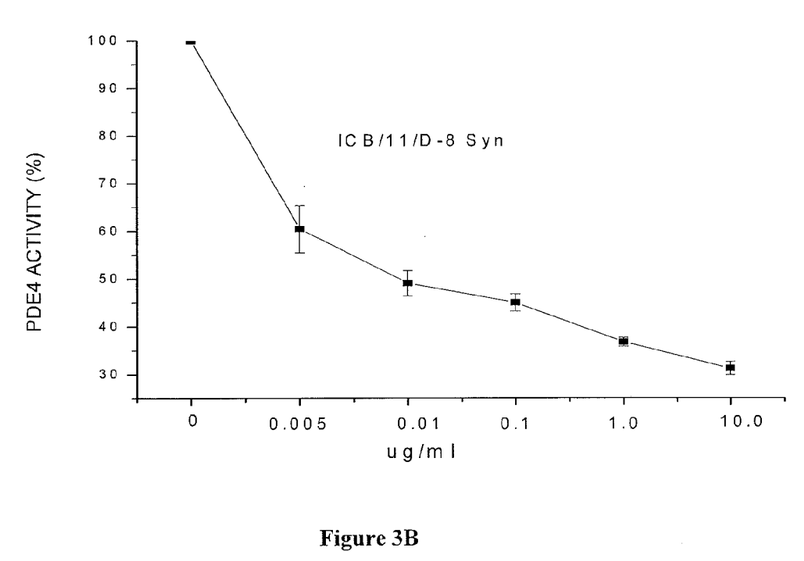
FIG. 3B illustrates the inhibition of PDE 4 activity by synthetically prepared compound I based on natural product.

As shown in FIG. 3, with increasing dose of the compound (compound I) of natural origin the PDE 4 activity was inhibited significantly. The extent of inhibition of PDE 4 activity by compound I is comparable to known PDE 4 inhibitor, rolipram. The IC50 of compound I is 20 µM. As presented in FIG. 3, the synthetically prepared compound I also inhibited PDE 4 activity in a dose dependent manner and the IC50 is 50 nM. The results are presented in FIG. 3.

The % inhibition of compounds is indicated in Table A

TABLE A

| Compound | Dose | % of Inhibition |
|---|---|---|
| I | 10 µg/ml | 73.1 |
|  | 1 µg/ml | 34.7 |
|  | 0.1 µg/ml | 1.4 |
| V | 10 µg/ml | 44.2% |
|  | 1 µg/ml | 11.80% |
|  | 0.1 µg/ml | 0 |

Example 9

Protocol for In Vivo Test in Asthma Model in Mice

Step 1: Sensitization and Challenge

Mice were sensitized with 0.2 ml PBS containing 50 µg ovalbumin (OVA) (Sigma, USA) and 4 mg aluminum hydroxide in saline intraperitonially (i.p.) on days 0, 7 and 14 as shown in scheme 2. Sham group mice were sensitized with only alum dissolved in PBS. From day 21 to 30, mice were exposed to aerosol of OVA (3%) inhalation 25 minutes daily in a Plexiglas chamber (20×20×10 cm$^3$). The aerosol was generated by a nebulizer (OMRON CX, model) with an airflow rate of 9 L/minute. Sham group mice were challenged with PBS alone.

Step 2: Mice Grouping and Treatment with Compound I

There were two set of experiments: i) screening experiments with different concentrations of Compound I and ii) confirmatory experiments. For screening experiments, mice were divided randomly after acclimatization into 6 groups, each group (n=4-5) was named according to sensitization/challenge/treatment: Group I was alum sensitized, saline challenged and treated with vehicle (SHAM/SAL/VEH), group II was OVA sensitized, OVA challenged and treated with DMSO as vehicle (OVA/OVA/VEH), group III, IV, V were OVA sensitized, OVA challenged and treated with 0.1, 1 and 10 mg/kg Compound I and group VI was OVA sensitized, OVA challenged and treated with 0.75 mg dexamethasone (OVA/OVA/DEX). Compound I was dissolved in DMSO. So DMSO was used as a vehicle. Compound I or DEX was given orally twice per day in the volume of 10 Confirmatory experiments were done once with 0.1 mg/kg Compound I with 6 mice in each group.

Step 3: Determination of Airway Responsiveness

Airway responsiveness was measured by barometric plethysmography using whole-body plethysmography (WBP; Buxco, Troy, N.Y.) 12 hours after last saline or ovalbumin challenge. At the time of measurement the animals were awake and breathing spontaneously. Enhanced pause (Penh) to methacholine as measured using barometric plethysmography is a valid indicator of bronchoconstriction in mice and can be used to measure AHR. Baseline pen H was taken initially, and then PBS followed by increasing concentrations (0-16 mg/ml) of methacholine was nebulized through an inlet of the main chamber for 3 min. Readings were taken and averaged for 5 minutes from the starting time of nebulisation. Airway responsiveness to MCh was evaluated by the concentration of MCh required to increase the Pen H to twice the baseline value (MCh PC$_{200}$). The results are presented in FIG. 4. The level of MChPC200 was decreased significantly in asthmatic controls (OVA/OVA/VEH) compared to normal control mice (SHAM/PBS/VEH). This indicates that OVA/OVA/VEH mice have developed marked bronchoconstriction. However, treatment with Compound I significantly attenuated the decrease in MChPC200 and maximum effect was found with 10 mg/kg dose (FIG. 4). This reduction was comparable with steroid, dexamethasone treatment (OVA/OVA/DEX).

Example 10

Histological Analysis of Lung Inflammation

To determine the effect of Compound I on airway inflammation, histopathological analysis of formalin fixed, paraffin embedded lung sections was performed. The excised lung portion was fixed in 10% buffered formalin. The fixed, paraffin embedded tissue were sectioned into 4 µm sections and stained with Hematoxylin & Eosin (H&E) to assess inflammation The following features were observed i) SHAM/PBS/VEH mice showed normal architecture of lung, ii) OVA/OVA/VEH mice showed dense infiltration of inflammatory cells including eosinophils, mononuclear cells such as monocytes and lymphocytes, neutrophils in perivascular and peribronchial regions but alveolar regions were free from any infiltrated cells. However, Compound I treatment reduced both perivascular and peribronchial inflammation in a dose dependent manner. The results are presented in FIG. 4B.

Example 11

Determination of Pharmacokinetics

Treatment of animal: Healthy swiss mice of both the sexes (25-30) were used. The animals were kept (3/cage) under controlled conditions (temp 26±2° C.; relative humidity 50±5%; 12 h light/dark cycle) and maintained on pelleted rodent diet (i.v.route). Ashirwad Industries Ltd. Chandigarh, India). Water was provided ad libitum. Compound I was solubilised in 2% gum acacia by trituration and diluted with normal saline to obtained desired concentration. The compound was administered orally (20 mg/kg BW) or via intravenous route (10 mg/kg bw).

Sampling time: Blood samples were collected at 0, 5, 15 and 30 min, and 1, 2, 4, 6, 8, 16 and 24 hrs post-administration after oral/iv route in pre-labeled heparinised tubes and centrifuged (3500 rpm×10 minutes) to obtain the plasma. A total of 6 animals were used per time point.

Sample Preparation (i) Aliquots of plasma (250 ul) were mixed with ethyl acetate (3 ml), vortexed for two minutes (2500 rpm) and centrifuged at 5000 rpm for 10 min. The organic layer was collected and evaporated to dryness using solvent evaporator (Model: SPD 111V, Thermo Electron Corporation, MA). The dried samples were reconstituted in mobile phase for HPLC analysis.

(2) Calibration standards were prepared from aliquots of plasma collected from untreated animals which were spiked with molecule I (0.25 μg-10 μg/ml). These were used to draw calibration curves which were found to be linear ($r^2=0.9998$). The extraction efficiency of the molecule from plasma matrix was 90-93%.

HPLC determinations HPLC determinations were done on Thermofinningan chromatograph (Model: SpectraSystem SCM 1000 equipped with quaternary pump P-4000; autosampler AS 3000; UV 6000 LP): diode array detector). Molecule D8 was run under the following conditions:

Column: RP-8 (5 um); Mobile Phase: Acetonitrile:Water (51:49); Wavelength: 272 nm Flow Rate: 1 ml/min; Retention time: 8.035 min; The lower limit of detection (LOD): 3.5 ng/ml; limit of quantitation (LOQ): 10 ng/ml.

Bioavailability indices. A concentration-time curve for Molecule D8 was established and pharmacokinetic parameters ($C_{max}$, $T_{max}$, $AUC_{0-24}$, Clerance (Cl) and Volume of Distribution (vd) were determined by using a software (PK Solutions version 2.0; Summit Research Services, USA).

Figure 5A:
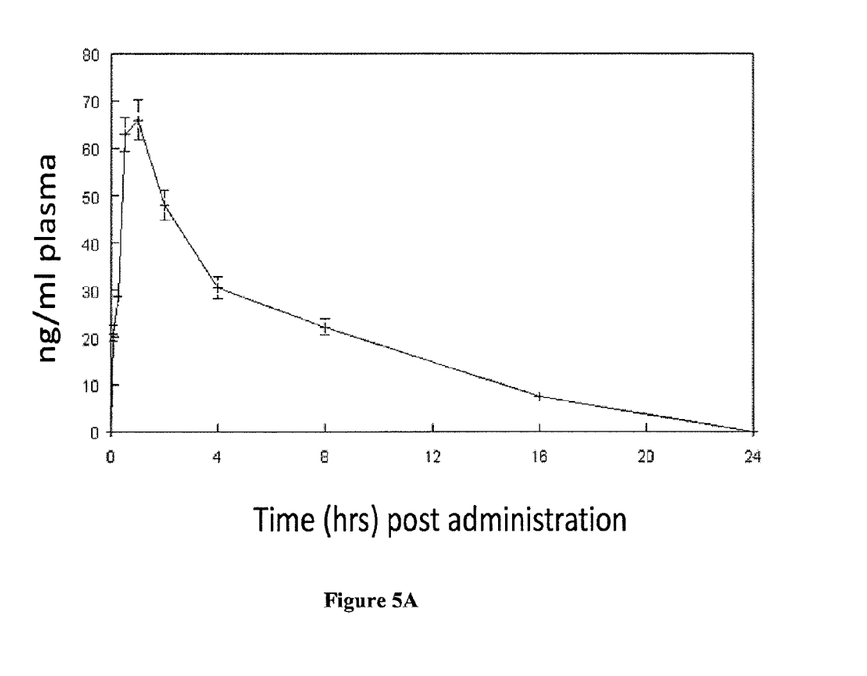
FIG. 5A Pharmacokinetics of the compound I administered through oral route.
Figure 5B:
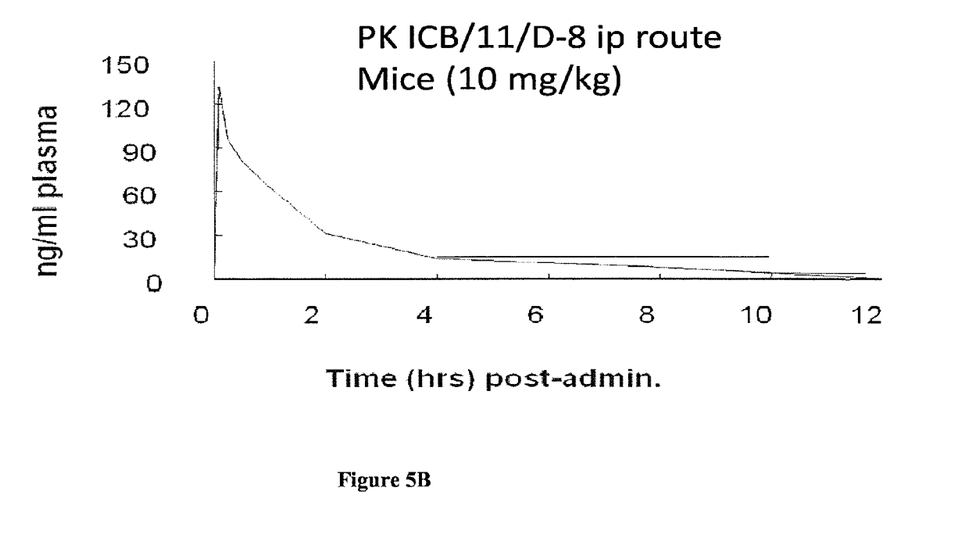
FIG. 5B Pharmacokinetics of the compound I administered through intravenous route in mice.

Absolute bioavailability was determined using the following formula: $AUC_{oral} \times dose_{iv}/AUC_{iv} \times Dose_{oral}$. The results are presented in FIG. 5.

Organ Distribution of ICB/11/D-8 (ug/100 mg tissue, N=4 mice, 50

|  | 0.5 hr | 2 hr | 4 hr | 12 hr |
|---|---|---|---|---|
| Brain | 0.23 | 2.67 | 4.33 | 0.36 |
| Liver | 8.95 | 16.78 | 11.05 | 1.25 |
| Lungs | 12.22 | 27.32 | 8.07 | 0.67 |
| Spleen | 12.27 | 13.99 | 5.25 | 0.91 |
| Heart | 18.52 | 26.26 | 16.81 | 3.22 |
| Kidneys | 13.51 | 17.12 | 10.52 | 1.58 |
| Stomach | 37.80 | 68.93 | 22.69 | 4.33 |
| Intestine | 10.50 | 16.75 | 12.38 | 2.55 |
| Testes | 16.76 | 31.31 | 5.88 | 0.78 |
| Urine/ml | 2.6 | 6.56 | 4.07 | — |

Example 12

Determination of Safety Pharmacology of Compound I

Spontaneous Motor Activity (Mice)

Each animal was placed in activity cage (Ugo Basile, Comerio, Italy) with a grid floor equipped with a recording device, and activity counts were recorded for 5 mins. Counts indicate spontaneous coordinate activity, meaning movement of experimental animals within a specified duration of time. A comparison of mean counts (recorded at 15 min. intervals for a period of 2 hr.) between control (untreated) and D8 treated mice was made [Kim H-W, Known Y-B, Ham T-W, Roh D-H, Yoon S-Y, Kang S-Y, Yang I-S, Han H-J, Lee H-J, Beitz A J, Lee J-H., General pharmacological profiles of bee venom and its water soluble fractions in rodent models. J. Vet. Sci. 5 (2004) 309-318].

TABLE 1

Effect of Compound I on Spontaneous motor activity in mice

| Group | Treatment (p.o.) | Activity (counts/min) | |
|---|---|---|---|
| | | 0 mins. | 60 mins. |
| Control | — | 22.4 ± 5.41 | 19.7 ± 3.83 |
| Compound I | 12.5 | 24.9 ± 6.18 | 18.9 ± 7.97 |
| | 25 | 20.4 ± 4.14 | 14.9 ± 5.02 |
| | 50 | 20.2 ± 5.59 | 16.8 ± 5.33 |

N = 5; Adult Mice (5/gr: both sexes)

Group of five mice were orally administered drug or vehicle. Each animal was then placed immediately in an activity cage (Ugo Basile, Comerio, Italy) with a grid floor equipped with a recording device, and activity counts were recorded for 5 mins.

Compound I (12.5, 25 and 50 mg/kg) administered orally to different groups of mice, there was found no significant change in spontaneous motor activity in any treated groups as compared to the control group Analgesic Activity (Mice)

Analgesic activity was carried out by Hot Plate method. The response time for paw licking or jumping on the heated plate of analgesiometer (55±1° C.). (Socrel, Ugo Basile, Italy) was taken as the reaction time. A comparison of reaction time (in seconds) between control (untreated) and Compound I treated mice was made for a group of 6 animals in each test group [Eddy, N B., Leimbach, D., Synthetic analgesics, II. Dithienylbutenyl- and dithienylbutylamines. J. Pharmacol. Exp. Ther. 107 (1953) 385-393].

TABLE 2

Analgesic activity of Compound I by hot plate method in mice

| 1 | Dose (mg/kg; p.o.) | Reaction time (Seconds) | |
|---|---|---|---|
| | | 0 hr | 1 hr |
| Control | — | 15.78 ± 3.25 | 10.38 ± 3.0 |
| ICB/11-D8 | 12.5 | 11.08 ± 1.60 | 10.62 ± 1.64 |
| | 25 | 13.58 ± 2.15 | 14.62 ± 4.67 |
| | 50 | 14.38 ± 1.87 | 14.34 ± 1.07 |

N = 5

The time for hind paw licking or jumping on the heated plate of analgesiometer (Socrel, ugo basile, Italy) was taken as the reaction time.

Compound I (12.5, 25 and 50 mg/kg) administered orally did not show any significant change in the reaction time of mice on a hot plate maintained at 55±1° C.

Electric Shock Induced Convulsions (Mice)

Convulsion were induced by a single electroshock (50 Hz in frequency, 0.5 ms pulse width, 50 mA current for 0.3 s) applied through bi-polar electrodes attached to the ear pinna on both side using a pulse generator (Ugo Basile, Italy). The convulsive activity (determined by loss of tonic extensor seizure) was recorded in control (untreated) and Compound I were treated (before electro-shock application) animals [Achliya, G S, Wadodkar, S G, Darle, A K., Evaluation of CNS activity of Bramhi Ghrita. Indian J. Pharmacol. 37 (2005) 33-36].

TABLE 3

Effect of Compound I on Electric shock induced convulsions in mice

| Treatment | Dose (mg/kg; p.o.) | Convulsions | | Mortality |
|---|---|---|---|---|
| | | Tonic | Clonic | |
| Control | — | 5/5 | 5/5 | 1/5 |
| Compound I | 12.5 | 5/5 | 5/5 | 1/5 |
| | 50 | 5/5 | 5/5 | 0/5 |
| | 100 | 5/5 | 5/5 | 0/5 |
| Phenobarbitone | 30 | 0/5 | 0/5 | 0/5 |

Anti-convulsant activity was measured by electric shock induced seizure. Five Swiss mice were used for one dose of drug. Convulsion were induced by a single electroshock (50 Hz in frequency, 0.5 ms pulse width, 50 mA current for 0.3 s) applied through bi-polar electrodes attached to the ear pinna on both side by a pulse generator (Ugo Basile, Italy) Test drug were administered orally 60 min before electroshock application, and convulsive activity was determined by loss of tonic extensor seizure.

Compound I (12.5, 25 and 50 mg/kg) administered orally and the control group exhibited convulsions on application of electric shock. Therefore no anti-convulsant activity was exhibited by different doses of Compound I. On the contrary in phenobarbitone (positive control) treated group a significant anti-convulsant activity was observed where animals were protected from convulsions induced by maximal electric shock.

Charcoal Meal Transit Time (Mice)

A of charcoal suspension (20 ml/kg prepared as a 5% solution in 10% gum acacia) was administered perorally 60 min after D8 administration (perorally). After 30 min, charcoal meal administration small intestines were excised and aligned parallel to a ruler. Ratio of the distance traveled by the charcoal meal to the total length of the small intestine was determined for the control (untreated) and Compound I treated mice [Ali, B. H. Bashir, A A. The effect of alpha 2-receptor agonists and antagonists on gastro-intestinal transit time. Clinical and Experimental Pharmacology and Physiology, 20 (1993) 1-6].

The results shown depict no significant change in charcoal powder transporting ratio with different doses of Compound I (12.5, 25 and 50 mg/kg) in comparison with the control group.

TABLE 4

Effect of Compound I on charcoal meal transit time in mice

| Treatment | Dose (mg/kg; p.o.) | % Transport (Mean ± SEM) |
|---|---|---|
| Control | — | 82.7 ± 3.5 |
| Compound I | 12.5 | 74.15 ± 3.4 |
| | 25 | 76.6 ± 6.7 |
| | 50 | 77.12 ± 1.49 |
| Atropine sulphate | 0.1 (i.p.) | 41.7 ± 2.52* |

N = 5

Bile Secretion (Rats)

Rats were anaesthetized with urethane (25% w/v; 0.6 ml/100 g bw, ip). A catheter was placed in the jugular vein for Compound I administration. Abdominal cavity was opened by midline incision and the common bile duct was cannulated to measure the biliary secretion which was collected over 2 hours duration. The total bile excreted was compared between control (untreated) and Compound I treated rats [Shetler, T., Bendele, A., Buening, M., Clemens, J., Colbert, W., Deldar, A., Helton, D., Mc Grath J., Shannon, H., Turk, J., Williams, P., General Pharmacology of Loracarbef in Animals. Arzneim-Forsch./Drug Res. 43 (1993) 1-6]. Compound I (25 and 50 mg/kg) administered intravenously has shown no significant change in the mass of bile collected as presented in Table 5.

TABLE 5

Effect of Compound I on bile secretion in rats

| Treatment | Dose (mg/kg; i.v.) | Bile (grams ± SEM) | |
|---|---|---|---|
| | | Before | After |
| Compound I | 25 | 1.285 ± 0.049 | 1.390 ± 0.06 |
| | 50 | 1.305 ± 0.145 | 1.125 ± 0.125 |
| Control | — | 1.486 ± 0.121 | 1.325 ± 0.088 |

N = 3

Pentobarbitone Induced Sleeping Time (Mice)

Compound I was administered to mice perorally. One postadmin. of D8 mice mice were administered with sodium pentobarbitone (50 mg/kg, ip). Sleeping time (No righting reflex) (in min) was determined for the control (untreated) and D8 treated animals [Montilla, M P., Cabo, J., Navarro, M C., Risco, S., Jimmenez R S., Aneires, J., The protective and curative action of Withania frutescens leaf extract against $CCl_4$-induced hepatotoxicity. Phytother. Res. 4 (1990) 212-215]. ICB11//D8 administered orally at 12.5, 25 and 50 mg/kg did not show any significant increase or decrease while as Positive control chlorpromazine (1 mg/kg, i.m.) treated group showed a significant increase in sleeping time in mice in comparison to the control group.

TABLE 6

Effect of Compound I on pentobarbitone induced sleeping time in mice

| Treatment | Dose (mg/kg; p.o.) | Sleeping Time (Minutes ± SEM) |
|---|---|---|
| Pentobarbitone | 50 (i.p) | 75.6 ± 9.4 |
| Compound I | 12.5 | 109.8 ± 52.7 |
| | 25 | 117 ± 53.4 |
| | 50 | 109.8 ± 8.2 |
| Chlorpromazine | 1 (i.m.) | 325 ± 15* |

Determination of Blood Pressure, Heart Rate and Respiratory Rate

Male wistar rats of approximately 6 months of age were anaesthetised with a mixture of ketamine (40 mg/kg) and xylazine (5 mg/kg) and fitted with TL11M2-C50PXT telemetry transmitters (Data Sciences Intl., St. Paul, Minn., USA) in the peritoneal cavity by performing surgery. Experiments were performed 15 days after surgery. Individual rats were placed in plastic cage on top of a receiver (RLA 2000, Data Science) for the measurement of systolic BP, diastolic BP, Heart rate and respiratory rate. The signals from the transmitters were received by two RLA 2000 receivers and transmitted via a Data Exchange Matrix to a Dataquest PCI card CQ 2240 in the computer. The data were interpreted by the Dataquest program A.R.T. version 2.2 Gold Version. The data was recorded from 1 hour before and upto 4 hours after drug treatment (Guiol, C., Ledoussal, C., Surge, J M., A radiotelemetry system for chronic measurement of blood pressure and heart rate in the unrestrained rat validation of the method. Journal of Pharmacological Toxicological Methods. 28 (1992) 99-105]. Results presented in Table 6. The results show no significant change in blood pressure, heart rate and respiratory rate of the rats before and after drug treatment

TABLE 7

Effect of Compound I on blood pressure, heart rate and respiratory rate

| Treatment | Dose (mg/kg i.v.) | Observation | Observation time | | | | |
|---|---|---|---|---|---|---|---|
| | | | 0 mins | 1 hr | 2 hr | 3 hr | 4 hr |
| Compound I | 50 | SBP | 112 ± 2.89 | 115.4 ± 3.6 | 114.5 ± 2.8 | 110.2 ± 4.5 | 108.7 ± 5.2 |
| | | DBP | 71.7 ± 10.2 | 82.1 ± 4.5 | 77.5 ± 6.07 | 78.5 ± 8.1 | 75.9 ± 8.2 |
| | | HR | 242.1 ± 9.7 | 309.1 ± 45.9 | 261 ± 13.8 | 272.7 ± 17.5 | 273.1 ± 17.06 |
| | | RR | 89.4 ± 1.4 | 85.77 ± 8.9 | 89.5 ± 2.56 | 84.5 ± 3.5 | 96.3 ± 2.1 |

N = 3; ANOVA

Example 13

28 d Sub-Acute Oral Toxicity of Compound I in Mice

The study was performed according to the guidelines laid in OECD TG 407. Young healthy adult mice (Balb/c) weighing between 28 to 35 g were employed and randomly assigned to the control and treatment groups and kept in their cages for at least five days prior to the start of the treatment to allow for acclimatisation to the laboratory conditions. 10 animals (five female and five male) were used at each dose level. Local standards of laboratory animal care were maintained. The temperature in the experimental animal room was maintained at 24° C.±3° C. and the relative humidity between 40 to 60% with 12 hours artificial light and 12 hours dark photoperiod. For feeding, conventional sterile pellet diets (Nay Chetan) with an unlimited supply of RO drinking water was given. A sample of the diet was retained until finalisation of the report. Animals were housed in small groups of 5 of the same sex.

The test substance (Compound I) was insoluble in water and hence suspended in ground-nut oil (vehicle) and administered daily by gavage in doses of 187, 93, 46 and 0[vehicle only] mg/kg body weight to several groups of experimental animals for a period of 28 days. Blunt ended canula was used for gavaging. During the period of administration of Compound I, the animals are observed closely (30 minutes cage side observation), each day for signs of toxicity till the day of sacrifice. Weights of animals and measurements of food consumption were made once in a week.

Experimental animals were sacrificed on day 29. Before sacrifice, blood was drawn from the retro-orbital sinus of mice with the help of heparinised capillary tubes and split in to two parts. Part taken in tubes containing EDTA was used for hematological studies with the help of Automatic Hematology Analyzer (Medonic). The other part was allowed to clot for 2 h and serum separated by centrifugation at 3000 rpm for 5 min, and subsequently used for clinical biochemistry and immunoglobuling profiling. Post sacrifice, the individual organs were dissected out, weighed and percentage relative organ weights determined. Spleen, lymphnode and bone marrow cell viability were judged by trypan blue dye exclusion test.

TABLE 8

Hematological profile of mice treated with Compound I

| Parameters | Vehicle control | 187 mg/kg | 93 mg/kg | 42 mg/kg |
|---|---|---|---|---|
| RBC (×$10^6$/mm$^3$) | 8.72 ± 0.62 | 8.6 ± 0.67 | 8.52 ± 1.4 | 7.29 ± 1.46 |
| WBC ($10^3$/mm$^3$) | 5.3 ± 3.7 | 5.9 ± 4.1 | 5.9 ± 1.4 | 6.7 ± 1.2 |
| PLT (× $10^3$/mm$^3$) | 449 ± 79 | 472 ± 65 | 426 ± 43 | 439 ± 76 |
| HGB (g/dL) | 13.6 ± 1.3 | 13.2 ± 1.8 | 12.8 ± 2.4 | 9.47 ± 1.7 |

RBC: red blood corpuscles;
PLT: platelet count;
WBC: White blood corpuscle count;
HGB: Hemoglobin concentration;

Clinical Biochemistry Test

The blood left after the hematological studies were allowed to clot for 2 h and serum separated by centrifugation at 3000 rpm for 5 min and subsequently used for clinical biochemistry. Details of the clinical biochemistry are given below in table II. All the values of different parameters are within the normal range except SGOT which is marginally higher than the normal range in mice treated with 187 mg/kg Compound I and may be ignored. Similarly, glucose is marginally higher than the normal range in mice treated with 93 mg/kg of Compound I and may be ignored. However, at a dose 187 mg/kg of Compound I glucose level is much higher than the normal range.

TABLE 9

Clinical biochemistry of Compound I treated mice

| Parameters | Vehicle control | 187 mg/kg | 93 mg/kg | 42 mg/kg |
|---|---|---|---|---|
| Protein (g/dL; 6-9) | 7.61 ± 1.8 | 7.27 ± 0.85 | 8.73 ± 2.8 | 7.93 ± 1.33 |
| SGPT(U/L; <22 @25° C.) | 6.69 ± 1.31 | 15.83 ± 2.32 | 10.2 ± 2.9 | 18.54 ± 2.1 |
| SGOT (U/L; 19@25° C.) | 10.2 ± 0.61 | 20.2 ± 0.85 | 12.9 ± 1.92 | 15.51 ± 3.6 |
| Bilirubin (mg/dL; <1.1) | 0.66 ± 0.054 | 0.91 ± 0.057 | 0.17 ± 0.068 | 0.74 ± 0.08 |
| Glucose (mg/dL; 55-130) | 109 ± 17 | 183 ± 20 | 133 ± 13 | 127 ± 17 |

Serum concentrations of total IgG and IgM were measured by ELISA and Cell mediated immunity was measured in terms of % increase in paw volume in mice sensitized with SRBC.

Immunotoxicity in Mice Treated with Compound I.

No significant changes were observed in the viability of bone marrow cells, splenocyte and lymph node lymphocyte in the Compound I treated mice in comparison to sham treated control as judged by trypan blue dye exclusion test. Based on our ELISA results, serum concentrations of total IgG and IgM in mice treated with Compound I were similar to sham control. Cell mediated immunity was measured in terms of % increase in paw volume in mice sensitized with SRBC. We observed insignificant changes in the DTH response in mice treated with Compound I in comparison to sham treated control (Table IV).

TABLE 10

Immunotoxicity profile in mice treated with Compound I

|  | Veh. Control | 187 mg/kg | 93 mg/kg | 47 mg/kg |
|---|---|---|---|---|
| % viability |  |  |  |  |
| LN | 96.2 ± 4.2 | 97.4 ± 3.9 | 96.5 ± 4.6 | 95.9 ± 5.4 |
| Spleen | 97.3 ± 6.4 | 98.4 ± 4.4 | 95.4 ± 5.3 | 96.8 ± 4.8 |
| BM | 98.6 ± 5.6 | 94.67 ± 4.9 | 96.8 ± 4.6 | 97.3 ± 3.5 |
| Total Ig |  |  |  |  |
| IgG (mg/mL) | 3.1 ± 0.85 | 2.9 ± 0.56 | 3.6 ± 1.26 | 3.1 ± 0.85 |
| IgM | 1.56 ± 0.23 | 1.04 ± 0.34 | 1.12 ± 0.33 | 1.48 ± 0.12 |
| CMI |  |  |  |  |
| DTH (% increase in paw vol) | 16.7 ± 5.3 | 17.4 ± 6.6 | 19.2 ± 6.3 | 17.23 ± 4.4 |

Figure 6A:
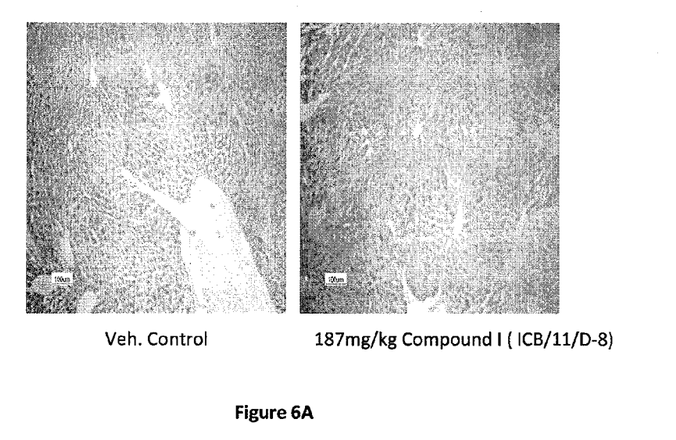
FIGS. 6A and 6B depicts histological analysis of the tissue after treatment with compound I. A. Liver. B. Kidney tissue.

Histopathology was carried out on vital organs by fixing organs in 10% buffered formalin saline for 72 h followed by washing, dehydrating and embedding on paraffin wax. Paraffin blocks were sectioned (4-5µ tick), deparaffinised and stained with hematoxylin and eosin for viewing and photography under microscope (Nikion, Japan). Histopathology was performed in the control and high dose groups unless mentioned otherwise. The results are presented in FIG. 6.

Figure 6B:
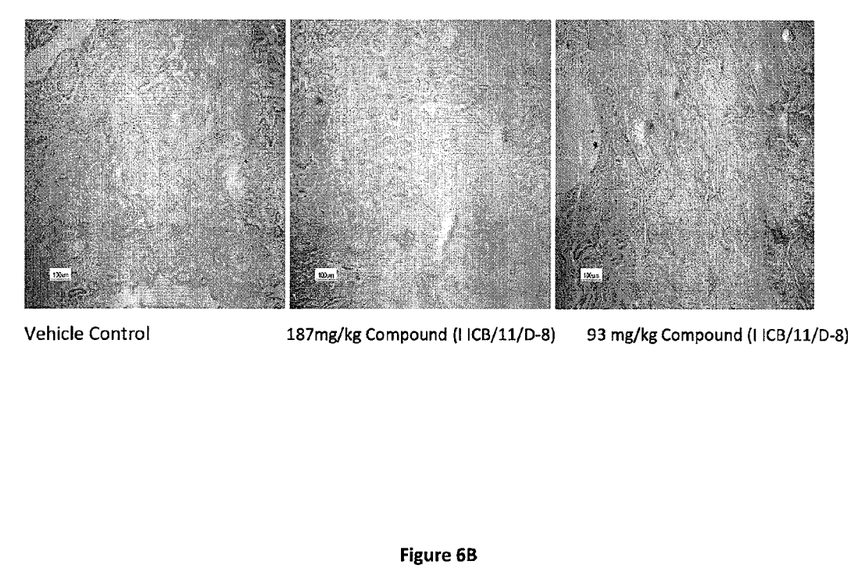

The corticular region of the sham treated kidney showed enormous number of Bowman's capsules that were uniformly distributed throughout the corticular region. Majority of the capsules were oval and round in shape but few elliptical shaped Bowman's capsules were also encountered. In the kidney of mice treated with 187 mg/kg Compound I, sign of necrosis in the corticular region was observed but not in kidney of mice treated with 93 mg/kg Compound I.

ADVANTAGES OF THE INVENTION

The main advantages of the present invention are:
1. Present invention provides compounds of herbal origin relevant to treatment, relief and remedy of asthma/COPD.
2. It also provides a method of isolation of novel phosphodiesterase 4 (PDE 4) inhibitor from herbal source, therapeutically effective for the treatment of asthma and asthma related respiratory diseases.
3. It also provides methods of synthesis of novel PDE 4 inhibitor of herbal origin and their derivatives and their evaluation is to have more therapeutic accessibility to the compounds presented in the invention.
4. It is also provides the novel PDE 4 inhibitors and their analogues.
5. It also provides novel process routes for the synthesis of said novel PDE 4 inhibitor that exhibits significant anti-asthma activity.
6. Present invention provides novel process routes to the PDE 4 inhibitor of herbal origin using commercially available reagent and shorter chemical sequence.
7. Present invention provides non-toxic PDE-4 inhibitor which might be useful for the treatment of asthma.
8. Present invention provides PDE 4 inhibitor which inhibits the signalling pathway such as expression of intercellular adhesion molecule or vascular cell adhesion molecule which is crucial for asthma pathogenesis.

We claim:

1. A method for treating bronchial asthma, chronic obstructive pulmonary disease (COPD), or both, comprising administering to a patient in need of such treatment a therapeutically-effective dose of a compound, said compound being from general formula 1 or a salt thereof, and wherein said compound is optionally administered with one or more pharmaceutically acceptable excipients General formula I wherein
$R_1$=H or $OCH_3$;
$R_2$=CHO, $CH_3$, $CH_2OH$ or $CH_2OAC$;
$R_3$=H or $OCH_3$;
$R_4$=H, OH or $OCH_3$.

2. The method according to claim 1, wherein said compound is selected from the group consisting of 1-methoxy-3-formylcarbazole, 3-methyl-6-methoxycarbazole, 1-methoxy-3-hydroxymethylcarbazole, 1-hydroxy-3-formylcarbazole, 1-methoxy-3-methylacetoxycarbazole and 2,6-dimethoxy-3-methylcarbazole.

3. The method according to claim 1, wherein said administration is by an oral, intravenous or mucosal route.

4. The method according to claim 1, wherein said therapeutically-effective dose is between 1 to 10 mg/Kg body weight.

5. The method according to claim 1, wherein said compound inhibits phosphodiesterase-4 (PDE-4) enzyme activity in vitro by up to 90% at a dose of 0.001-10 µg/ml.

6. The method according to claim 1, wherein said compound is non toxic as determined by measuring an indicator selected from the group consisting of: spontaneous motor activity; analgesic activity; charcoal powder transportation ratio; bile secretion; pentobarbitone sleeping time; blood pressure; heart rate; respiratory rate; and viability of bone marrow cells, splenocytes or lymph node lymphocytes.

7. The method according to claim 1, wherein said compound is chemically synthesized or obtained from a herb.

8. The method according to claim 1, wherein the IC50 value of said compound is 50 nM.

* * * * *